United States Patent [19]

Rouet

[11] 4,444,749

[45] Apr. 24, 1984

[54] COSMETIC COMPOSITIONS FOR THE HAIR

[76] Inventor: Jean M. Rouet, 1, Avenue Normandie-Niemen, Le Blanc-Mesnil (Seine et Oise), France

[21] Appl. No.: 974,446

[22] Filed: Dec. 29, 1978

Related U.S. Application Data

[63] Continuation of Ser. No. 869,099, Jan. 13, 1978, which is a continuation of Ser. No. 695,373, Jun. 14, 1976, abandoned, which is a continuation of Ser. No. 592,271, Jul. 1, 1975, abandoned, which is a continuation of Ser. No. 279,725, Aug. 10, 1972, abandoned, which is a continuation-in-part of Ser. No. 824,683, May 14, 1969, abandoned, which is a continuation-in-part of Ser. No. 365,483, May 6, 1964, abandoned.

[51] Int. Cl.$^3$ .................. A61K 7/06; A61K 31/74
[52] U.S. Cl. .................. 424/70; 424/DIG. 1; 424/DIG. 2; 424/47; 424/71; 424/78
[58] Field of Search .................. 424/DIG. 1, DIG. 2, 424/47, 70, 81, 78; 260/29.6 RW, 29.6 E

[56] References Cited

U.S. PATENT DOCUMENTS

| | | | |
|---|---|---|---|
| 2,821,521 | 1/1958 | Price | 260/78 |
| 2,977,334 | 3/1961 | Zopf et al. | 260/27 |
| 2,988,539 | 6/1961 | Cohen et al. | 260/78 |
| 3,130,127 | 4/1964 | Tarpey | 424/81 |

FOREIGN PATENT DOCUMENTS

| | | | |
|---|---|---|---|
| 1084440 | 6/1960 | Fed. Rep. of Germany | 424/71 |
| 1099737 | 2/1961 | Fed. Rep. of Germany | 424/71 |

*Primary Examiner*—Dale R. Ore
*Attorney, Agent, or Firm*—Cushman, Darby & Cushman

[57] ABSTRACT

Cosmetic composition for human hair containing water-soluble polyamine derivatives of maleic anhydride/ethylenic polymers.

4 Claims, No Drawings

COSMETIC COMPOSITIONS FOR THE HAIR

This application is a continuation of application Ser. No. 869,099, filed Jan. 13, 1978 which, in turn, is a continuation of Ser. No. 695,373, filed June 14, 1976 (now abandoned), which is a continuation of application Ser. No. 592,271, filed July 1, 1975, now abandoned, which is a continuation of Ser. No. 279,725, filed Aug. 10, 1972 (now abandoned), which is a continuation-in-part of Ser. No. 824,683, filed May 14, 1969 (now abandoned), which is a continuation-in-part of Ser. No. 365,483, filed May 6, 1964, now abandoned.

This invention relates to a cosmetic composition for treating living human hair.

Heretofore, compositions employed as fixatives or setting agents for living human hair which were derivatives of copolymers of maleic anhydride and an ethylenic monomer such as ethylene exhibited little affinity for the keratin which constitutes the hair, so that hair lacquers containing these copolymers did not adhere well and were rapidly removed under mechanical actions, such as brushing the hair. Consequently, hair sets produced with these setting agents were not as durable as desired.

It has now been found that the cosmetic composition of this invention, containing as it does the reaction product of a maleic anhydride-ethylenic copolymer with a polyamine, exhibits an improved affinity for keratin, retains a longer set and is more satisfactory for use as a hair-setting agent. It has also been found that this composition is usefully employed as a hair softening agent which imparts to the hair a greater sliding power, improves its appearance and renders the hair easier to comb.

More specifically, the cosmetic composition of the present invention comprises a solution in a solvent selected from the group consisting of water and an aqueous alcohol solution of a polymer having repeating units of the formula:

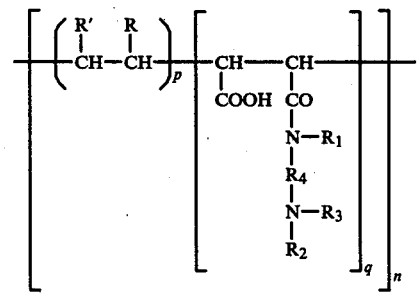

wherein R and R' each independently represent a member selected from the group consisting of hydrogen, $-CH_3O$, $-CH_3CH_2O$ and phenyl with the proviso that one of R and R' is hydrogen; $R_1$ and $R_2$ each represent lower alkyl having 1-4 carbon atoms; $R_4$ is alkylene containing 2-6 carbon atoms; $R_3$ is selected from the group consisting of lower alkyl containing 1-6 carbon atoms and $-R_4-N(R_2)_2$ wherein $R_2$ and $R_4$ have the meanings given above; the molar ratio p/q ranging between 1:1 to 1:0.7; and n is 2–10, said polymer being present in said composition in amounts of 0.5–10 percent by weight thereof and said composition having a pH of 3.5 to 10.

The above defined polymer can be prepared by reacting a linear copolymer of maleic anhydride and an ethylenic monomer in which the molar ratio of ethylenic monomer to maleic anhydride is from 1:1 to 1:0.7 with 1–10 moles of a polyamine having a primary or secondary amine group and one or more tertiary amine groups. At each stage of the reaction, the reactants are controlled so that the solubility of the resulting polymer in water or in a solution of alcohol and water is between 0.5–10% by weight.

The polyamine reactant has the formula:

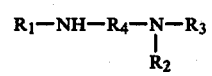

wherein $R_1$, $R_2$, $R_3$ and $R_4$ are defined above.

Representative polyamines used in the process of the present invention include a primary-tertiary amine, such as N,N dimethyl-1,2-ethylene-diamine, N,N-dimethyl-1,3-propylenediamine, N,N-diethyl-1,3-propylene diamine, N,N-dipropyl-1,3propylenediamine, N-propyl-N-methyl-1,3-propylenediamine, or N,N-dimethyl-1,4-butylenediamine; or a secondary-tertiary amine, such as N,N-dimethyl-N'-methylethylenediamine or N,N-dimethyl-N'-methylpropylenediamine. The compounds of the invention may be substituted by other amino or alkylene groups and there may be added to the reaction mixture other products which react with the anhydride function, for instance a primary or secondary amine or an alcohol. Where this is done it is recommended, in order that the reaction may take place with a good yield, to add to the mixture of reactants a tertiary amine in such a quantity that it represents the chemical equivalent of the primary or secondary amine or of the alcohol.

The copolymer employed for reaction with the polyamine is one of maleic anhydride and a ethylenically unsaturated monomer selected from the group consisting of ethylene, vinylmethyl ether, vinyl ether and styrene. The molar ratio of maleic anhydride to ethylenically unsaturated monomer is generally about 1:1, and said copolymer has a specific viscosity ranging from about 0.1 to 0.7 in a 1% solution in dimethyl formamide at 25° C.

The process for producing the polymers employed in the composition of this invention can be carried out in a homogeneous phase by using as a reaction medium a common solvent for the starting copolymer, for the polyamine and for the resulting polymeric product though, of course, the solvent must not be one which would react with those substances. Suitable solvents include acetone, dioxan and pyridine. The reactants should be present in an amount that will form polymers that have about 0.5–10% solubility in water or in an aqueous alcohol solution.

The process can alternatively be carried out in a heterogeneous medium by adding small amounts of the anhydride copolymer while stirring into an aqueous solution of the polyamine. The reactants should be present in amounts between about 0.5–10% and the anhydride copolymer addition to the reaction should be stopped either before or when the anhydride copolymer does not dissolve.

It is preferable to use proportions of anhydride copolymer and polyamine such that the amine and the anhydride functions of the copolymer are in equimolecular proportions. In this way excellent yields, for example in excess of 80%, can be obtained.

The polymeric products of the process of the present invention can be used as setting agents, when they have a solubility in solution between about 2% and 10% by weight in water or in an aqueous alcohol solution and are present in the composition in this concentration. They are also of use in cosmetic gels or creams as thickening agents.

The compositions of this invention can also be used as hair softening compositions when the polymers have a solubility in water or in an aqueous alcohol solution of 0.5–5% by weight and the polymers are present in the composition at this concentration.

At concentrations and solubilities below 0.5% and above 5% by weight the polymers do not soften the hair. At concentrations and solubilities below 2% by weight the polymers will not set the hair and at concentrations above 10% by weight the polymers are not effective hair setting agents.

Broadly the hair treating compositions of this invention contain 0.5–10% by weight of the soluble polymer in water or an aqueous alcohol solution and can have a pH ranging between 4.5–10. In general the specific pH used will influence the viscosity of the solution and the degree of solubility of the polymer in solution. For example, the viscosity of the polymers of Examples 2 and 3 below increases from a minimum at pH 4.5 to a maximum at pH 10. Also by converting the COOH group on the polymer to various salts modifies the solubility of the polymer and this modification allows the tailoring of the softening and/or the hair setting action of the composition to modify its effect on different types of human hair.

The preferred solvents are water and an aqueous alcohol solution in which the alcohol is a monohydric alkanol having 1–3 carbon atoms, such as methyl alcohol, ethyl alcohol, propyl alcohol and isopropyl alcohol.

The following examples are given to illustrate the invention and unless otherwise specified all parts and percentages are by weight.

EXAMPLE 1

Into 250 cc of a 2% solution of N-N-dimethylethylenediamine in water there are introduced in small successive portions, and with vigorous stirring, 8.85 g of a 1:1 copolymer of vinyl methyl ether and maleic anhydride having a specific viscosity of 0.1 to 0.5 in a 1% solution of the resin in dimethyl formamide at 25° C., care being taken that each successive portion of the copolymer is introduced only when the preceding portion has been completely dissolved in the amine solution. To the resulting viscous solution there is added a mixture of equal proportions of ethyl alcohol and ethyl acetate which precipitates a solid polymeric product.

This reaction product may be used as a softening agent by introducing it into a shampoo in a proportion of 0.5%. The shampoo thus treated provides a lather which is particularly soft to the touch and imparts to the hair high gloss and suppleness.

The product of this example may also be employed as a thickening agent for cosmetics, preferably in a concentration of about 2%, or as a hair softening agent at concentrations of 0.5–2% by weight.

EXAMPLE 2

To 250 cc of a 10% solution of N,N-diethyl-1,3-propylenediamine in acetone there are added 250 cc of an acetone solution containing 9.6% of a linear ethylenemaleic anhydride copolymer having a molecular ratio 1:1 and a specific viscosity of 0.1 in a 1% solution of the resin in dimethyl formamide at 25° C. It is observed that the reaction starts by itself with evolution of heat, and it is then sufficient to accelerate the reaction to complete it by heating to reflux temperature. The solvent is then removed from the resulting solution by evaporation, leaving as residue a polymeric product.

The product obtained may be successfully used as a softening agent in hair-setting lotions by dissolving it in an aqueous solution containing 3 to 30% ethyl alcohol. The resulting solution has about the same viscosity as the starting copolymer.

EXAMPLE 3

To 100 cc of an aqueous solution containing 6 weight percent N,N-dimethyl-1,3-propylenediamine, 4 weight percent butylamine and 4.2 g of pyridine there are added, in small quantities, 14.3 g of the 1:1 ethylene maleic anhydride copolymer used in Example 2, care being taken, before each successive portion of copolymer is added, that the preceding portion has been completely dissolved.

The solution thus obtained may be directly employed or the reaction product may be separated by evaporation and washed with ethyl alcohol so as to eliminate any unreacted amine. The polymeric product thus obtained may be employed in solution in water or in an aqueous alcohol solution, as defined above, to provide a hair-setting lotion. The concentration of polymeric product in such compositions may be, for example, from 2% to 5% in a hair-setting lotion comprising, for example, an aqueous solution containing 25% propyl alcohol.

EXAMPLE 4

18 g of a low molecular weight linear copolymer resulting from the copolymerization of 104 g of styrene and 88 g of maleic anhydride, having a molecular weight of approximately 1600, and a specific viscosity of about 0.67 in a 1% solution of the resin in dimethyl formamide at 25° C., are reacted with 100 cc of an aqueous solution containing 10% by weight N,N-diethylethylene-diamine, the copolymer being added in small successive portions and care being taken to ensure that each successive portion has dissolved before the next portion is added. The solution thus obtained may be employed in combination with the cosmetic compositions produced in accordance with Examples 2 and 3, for the same purpose and in the previously indicated concentrations. For example, it is possible to obtain an excellent hair-setting lotion by introducing into a 20% aqueous solution of ethyl alcohol 0.5% of the product of this Example and 1.5% of the product of Example 3.

EXAMPLE 5

The following anionic shampoo is prepared:

| | |
|---|---|
| sodium salt of technical grade lauryl ether sulphate (100% M.A.) | 7 g |
| polymer prepared in Example 1 | 0.5 g |
| lauric acid momoethanolamide | 2 g |
| alkylamine of lanolic acids, sold under the tradename LANAMINE | 2 g |
| methyl p.oxybenzoate | 0.1 g |
| tetrasodium salt of ethylene diamine tetracetic acid | 0.05 g |
| lactic acid q.s.p. | pH = 7.15 |
| water q.s.p. | 100 g |

EXAMPLE 6

The following amphoteric shampoo is prepared:

| | |
|---|---|
| lauroylcyclormidinium-1-ethoxyethionic acid-2 ethionic acid, disodium salt, sold under the tradename Miranol C2M | 30 g |
| polymer prepared in Example 1 | 0.5 g |
| lactic acid q.s.p. | pH = 3.5 |
| water q.s.p. | 100 g |

EXAMPLE 7

The following lotion for setting hair is prepared:

| | |
|---|---|
| polymer prepared in Example 1 | 5 g |
| hydroxyethyl-dimethyl-cetyl ammonium chloride | 1 g |
| perfume | 0.2 g |
| amino-methyl-propane-diol, q.s.p. for neutralization | |
| water, q.s.p. | 100 cc |

EXAMPLE 8

The following lotion for setting hair is prepared:

| | |
|---|---|
| polymer prepared in Example 4 | 3 g |
| perfume | 0.2 g |
| ethyl alcohol, q.s.p. | 20° |
| water, q.s.p. | 100 cc |

What is claimed is:

1. A shampoo comprising an aqueous solution of an anionic detergent and an effective amount of the reaction product resulting from the reaction in an aqueous medium of (i) a polymer of maleic anhydride and an ethylenically unsaturated monomer with (ii) a primary-tertiary polyamine or a secondary-tertiary polyamine.

2. A shampoo comprising an aqueous solution of an amphoteric detergent and an effective amount of the reaction product resulting from the reaction in an aqueous medium of (i) a polymer of maleic anhydride and an ethylenically unsaturated monomer with (ii) a primary-tertiary polyamine or a secondary tertiary polyamine.

3. A shampoo comprising an aqueous solution of a polymer having repeating units of the formula

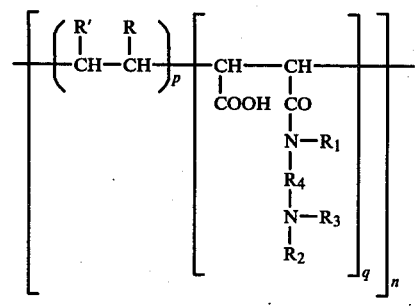

wherein
R and R' each independently represent a member selected from the group consisting of hydrogen, $-OCH_3$, $-OCH_2CH_3$ and phenyl with the proviso that one of R and R' is hydrogen;
$R_1$ represents hydrogen or lower alkyl having 1–4 carbon atoms;
$R_2$ represents lower alkyl having 1–4 carbon atoms;
$R_4$ is alkylene containing 2–6 carbon atoms;
$R_3$ is selected from the group consisting of lower alkyl containing 1–6 carbon atoms and $-R_4-N(R_2)_2$ wherein $R_2$ and $R_4$ have the meanings given above;
the molar ratio of p/q ranging between 1:1 to 1:0.7; and
n is 2–10;
said polymer being present in said composition in an amount of 0.5–10 percent by weight thereof, said composition having a pH of 3.5 to 10; and an anionic detergent.

4. A shampoo comprising an aqueous solution of a polymer having repeating units of the formula

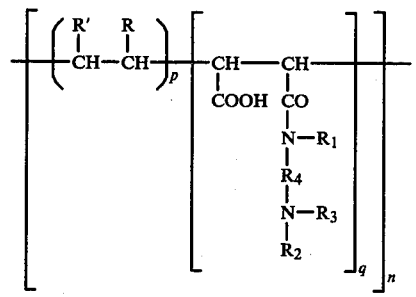

wherein
R and R' each independently represent a member selected from the group consisting of hydrogen, $-OCH_3$, $-OCH_2CH_3$ and phenyl with the proviso that one of R and R' is hydrogen;
$R_1$ represents hydrogen or lower alkyl having 1–4 carbon atoms;
$R_2$ represents lower alkyl having 1–4 carbon atoms;
$R_4$ is alkylene containing 2–6 carbon atoms;
$R_3$ is selected from the group consisting of lower alkyl containing 1–6 carbon atoms and $-R_4-N(R_2)_2$ wherein $R_2$ and $R_4$ have the meanings given above;
the molar ratio of p/q ranging between 1:1 to 1:0.7; and
n is 2–10;
said polymer being present in said composition in an amount of 0.5–10 percent by weight thereof, said composition having a pH of 3.5 to 10; and an amphoteric detergent.

* * * * *